(12) United States Patent
Lichtenberg et al.

(10) Patent No.: US 8,221,733 B2
(45) Date of Patent: Jul. 17, 2012

(54) VIRUCIDAL DISINFECTANT

(75) Inventors: Florian Lichtenberg, Deutschalnd (DE); Michael Lützeler, Deutschland (DE); Volker Ranft, Deutschland (DE)

(73) Assignee: Lonza AG, Basel (CH)

( * ) Notice: Subject to any disclaimer, the term of this patent is extended or adjusted under 35 U.S.C. 154(b) by 1130 days.

(21) Appl. No.: 10/501,395

(22) PCT Filed: Jan. 16, 2003

(86) PCT No.: PCT/EP03/00378
§ 371 (c)(1), (2), (4) Date: Aug. 18, 2004

(87) PCT Pub. No.: WO03/059062
PCT Pub. Date: Jul. 24, 2003

(65) Prior Publication Data
US 2005/0089496 A1      Apr. 28, 2005

Related U.S. Application Data

(60) Provisional application No. 60/349,994, filed on Jan. 23, 2002.

(30) Foreign Application Priority Data

Jan. 18, 2002 (EP) .................... 02001329

(51) Int. Cl.
*A61K 31/205* (2006.01)
*A01N 25/00* (2006.01)

(52) U.S. Cl. .................. 424/70.28; 424/405; 514/554; 514/642

(58) Field of Classification Search .................. 424/405, 424/70.28; 514/554, 642
See application file for complete search history.

(56) References Cited

U.S. PATENT DOCUMENTS

| | | |
|---|---|---|
| 5,908,854 A | 6/1999 | McCue et al. |
| 6,017,561 A * | 1/2000 | Zhou et al. .................. 424/486 |

FOREIGN PATENT DOCUMENTS

| | | |
|---|---|---|
| CN | 1222566 | 7/1999 |
| CN | 1258448 | 7/2000 |
| EP | 0799570 | 10/1997 |
| EP | 0848907 | 6/1998 |
| JP | 10/087410 | 4/1998 |
| WO | 94-22305 | 10/1994 |
| WO | 97-02028 | 7/1997 |
| WO | 98-20732 | 5/1998 |
| WO | 99-15012 | 4/1999 |
| WO | WO 00/03692 * | 1/2000 |
| WO | 02-23990 | 3/2002 |

OTHER PUBLICATIONS

Block, S.S., Disinfection, Sterilization and Preservation, (1991), Lea & Febiger, U.S., Chapter 25, Prince, H.N., et al. (Block).
Abstract, Database WPI, Section Ch, Week 199946, Derwent Publications Ltd., London, GB, An 1999-541231, XP 002190404.
Abstract, Database WPI, Section Ch, Week 199824, Derwent Publication's, Ltd., London, GB, AN 1998-266961.
Bundesgesundheitsbl., (1982), 25, 397-398.
Abstract, CA 134:168324, Database CA "Online!", (2002), Chemical Abstract Service, Columbus, OH, US, XP 002190403.
Bundasgesundheitsbl., (1983), 26, 413-414.

* cited by examiner

*Primary Examiner* — Robert A Wax
*Assistant Examiner* — Aradhana Sasan
(74) *Attorney, Agent, or Firm* — Hoffmann & Baron, LLP

(57) ABSTRACT

Process for utilizing the disinfectant composition as a virucidal agent. The disinfectant composition includes:
(a) an amine and/or quaternary ammonium salt of the general formula:

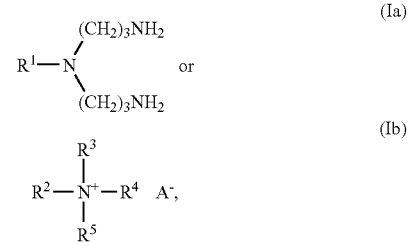

where $R^1$ is $C_{6-8}$-alkyl,
$R^2$ is benzyl or $C_{6-18}$-alkyl,
$R^3$ is $C_{1-18}$-alkyl or $—[(CH_2)_2—O]_nR^6$ where n=1-20,
$R^4$ and $R^5$ independently of one another are $C_{1-4}$-alkyl,
$R^6$ is hydrogen or unsubstituted or substituted phenyl, and
$A^-$ is a monovalent anion or one equivalent of a polyvalent anion of an inorganic or organic acid; and
(b) at least one alkanolamine of the general formula:

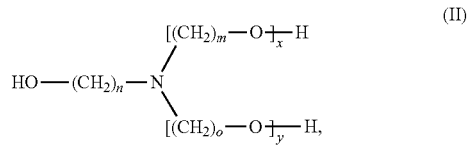

where n and, if present, m and o independently of one another have the value 2 or 3, and x and y independently of one another have the value 0 or 1, or a corresponding salt;
in the mass ratio of (a) to ( )b) of 20:1 to 1:20.

20 Claims, No Drawings

VIRUCIDAL DISINFECTANT

This application is a 371 national stage application of International (PCT) Application No. PCT/EP03/00378, filed on Jan. 16, 2003, that has priority benefit of European Patent Application No. 02001329.8, filed on Jan. 18, 2002, and U.S. Provisional Application No. 60/349,994, filed on Jan. 23, 2002.

The invention relates to the use of synergistic disinfectant compositions based on amines and/or quaternary ammonium salts as virucidal agents, in particular against polioviruses.

Numerous disinfectant and preservative compositions based on amines and/or quaternary ammonium salts are known. However, in general, in particular at relatively high dilution, these exhibit an unsatisfactory activity towards fungi, for example *Aspergillus niger* and viruses (in particular towards highly resistant viruses, for example polioviruses).

It was therefore an object of the present invention to provide disinfectant compositions based on amines and/or quaternary ammonium salts which exhibit good activity towards fungi and in particular towards viruses even at high dilution.

This object is achieved according to the invention by the use according to Claim 1.

The earlier application PCT/EP 01/10754 (published as WO 02/23990 A1) describes disinfectant compositions based on amines and/or quaternary ammonium salts and alkanolamines and their fungicidal properties. It has now surprisingly been found that such disinfectant compositions also display pronounced virucidal properties and, in particular, also good activity towards highly resistant viruses such as polioviruses. They are likewise active against other picornaviruses, for example ECHO viruses or corresponding animal pathogen viruses such as ECBO viruses, and also against parvoviruses, for example canine parvovirus.

The compositions comprise amines and/or quaternary ammonium salts of the general formula

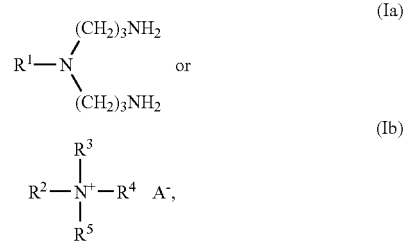

where $R^1$ is $C_{6-18}$-alkyl
$R^2$ is benzyl or $C_{6-18}$-alkyl
$R^3$ is $C_{1-18}$-alkyl or $-[(CH_2)_2-O]_nR^6$ where n=1-20
$R^4$ and $R^5$ independently of one another are $C_{1-4}$-alkyl
$R^6$ is hydrogen or unsubstituted or substituted phenyl
and $A^-$ is a monovalent anion or one equivalent of a polyvalent anion of an inorganic or organic acid;
and at least one alkanolamine of the general formula

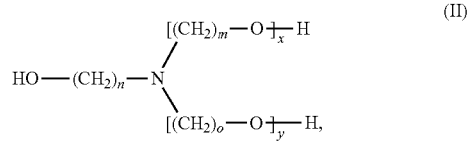

where n and, if present, m and o independently of one another have the value 2 or 3 and x and y independently of one another have the value 0 or 1, or a corresponding salt; in the mass ratio I:II of 20:1 to 1:20.

Alkyl, here and hereinafter, is taken to mean in each case unbranched or branched alkyl groups of the specified number of carbons, but preferably unbranched alkyl groups, and particularly preferably those having an even number of carbon atoms. In particular, this is also taken to mean the homologue mixtures derived from natural raw materials, for example "cocoalkyl".

Substituted phenyl is taken to mean, in particular, phenyl groups substituted with one or more $C_{1-18}$-alkyl groups and/or chlorine atoms. Suitable anions $A^-$ are in principle all inorganic or organic anions, in particular halide, for example chloride or bromide, or anions of low carboxylic acids, for example acetate, propionate or lactate.

The amine or quaternary ammonium salt (Ia/Ib) is preferably N,N-bis(3-aminopropyl)dodecylamine, N,N-bis(3-aminopropyl)octylamine, a didecyldimethylammonium salt, dioctyldimethylammonium salt, octyldecyldimethylammonium salt, dicocoalkyldimethylammonium salt, cocoalkyldimethylpoly(oxyethyl)ammonium salt, dicocoalkylmethyl-poly(oxyethyl)ammonium salt, decyldimethylpoly(oxyethyl)ammonium salt, didecylmethylpoly(oxyethyl)ammonium salt, octyidimethylpoly(oxy-ethyl)ammonium salt, dioctylmethylpoly(oxyethyl)ammonium salt, cocoalkytdimethylbenzylammonium salt, benzyldodecyidimethylammonium salt or benzyldimethylpoly(oxyethyl)ammonium salt or a mixture of two or more of these compounds. Particularly good results were achieved with didecyldimethylammonium salts.

Suitable alkanolamines (II) are in principle all ethanolamines and propanolamines, in particular monoethanolamine, diethanolamine, triethanolamine and 3-amino-1-propanol. Obviously, using mixtures of the said compounds is also within the scope of the invention. Particularly good results have been obtained using the compounds having a primary amino group, that is to say using monoethanolamine and 3-amino-1-propanol.

The mass ratio of amine (Ia) or quaternary ammonium salt (Ib) to alkanolamine (II) is preferably in the range from 1:5 to 5:1.

The disinfectant compositions used according to the invention preferably comprise water as solvent, if appropriate in combination with an organic solvent.

Preferably, the disinfectant compositions used according to the invention further comprise one or more aids selected from the group consisting of organic solvents, surfactants, complexing agents fragrances and colorants.

A preferred use of the disinfectant compositions is surface disinfection and instrument disinfection.

Further preferred fields of use are laundry disinfection and hand disinfection.

A further preferred use of the disinfectant compositions is the use in chemical toilets, for example on board aircraft and vehicles.

The examples below illustrate the implementation of the invention, and should not be taken to be a restriction to the embodiments described. All quantities given, where not otherwise specified, are in % by mass. The test microorganism used in each case was *Aspergillus niger* ATCC 16404. The effectiveness was determined, unless otherwise specified, using the method specified in CEN 1275.

EXAMPLE 1

A disinfecting cleaner formulation (concentrate) was prepared from:
5.0% didecyldimethylammonium chloride (50% strength solution)

2.0% N,N-bis(3-aminopropyl)dodecylamine
5.0% monoethanolamine
5.0% Genapol® 250 (tallow fatty alcohol polyglycol ether, 25 mol of ethylene oxide)
0.5% sodium metasilicate
0.5% sodium carbonate
2.0% methylglycinediacetic acid trisodium salt (Trilon® M; 40% strength solution)
water to 100%

The effectiveness was determined using a dilution (1 part of concentrate, 99 parts of water) at 20° C. and with a contact time of 15 min. The logarithm to base ten of the reduction in microorganism count was 4.1.

COMPARATIVE EXAMPLE 1

The procedure of Example 1 was followed, but with the difference that the monoethanolamine was replaced by the same amount of water. Under the same test conditions, the formulation was virtually inactive.

EXAMPLE 2

A disinfectant formulation (concentrate) was prepared from:
4.9% N,N-bis(3-aminopropyl)dodecylamine
4.0% monoethanolamine
2.0% Genapol® T250 (tallow fatty alcohol polyglycol ether, 25 mol of ethylene oxide)
5.0% Hostapur® SAS 30 ($C_{13-17}$ secondary n-alkanesulfonic acid, sodium salt)
2.0% ethylenediaminetetraacetic acid tetrasodium salt (40% strength solution)
0.7% ethylenediaminetetraacetic acid
water to 100%

The effectiveness was determined using a dilution (1 part of concentrate, 199 parts of water) at 20° C. and with a contact time of 15 min. The logarithm to base ten of the reduction in microorganism count was 4.3.

EXAMPLE 3

A disinfectant formulation (concentrate) was prepared from:
4.2% N,N-bis(3-aminopropyl)dodecylamine
2.0% didecylmethylpoly(oxyethyl)ammonium propionate (BARDAP 26)
4.0% monoethanolamine
2.0% Genapol® T250 (tallow fatty alcohol polyglycol ether, 25 mol of ethylene oxide)
5.0% Hostapur® SAS 30 ($C_{13-17}$ secondary n-alkanesulfonic acid, sodium salt)
2.0% ethylenediaminetetraacetic acid tetrasodium salt (40% strength solution)
0.7% ethylenediaminetetraacetic acid
4.0% butyl diglycol
water to 100%

The effectiveness was determined using a dilution (1 part of concentrate, 199 parts of water) at 20° C. and with a contact time of 15 min. The logarithm to base ten of the reduction in microorganism count was >4.4. In addition, the effectiveness was also determined using the method specified in CEN 1650 with a contact time of 15 min, a concentration of 1.0%, a water hardness of 30°fH and an organic load of 0.3% albumin. The logarithm to base ten of the reduction in microorganism count was >4.4.

EXAMPLES 4-19

Aqueous solutions were prepared from 0.5% alkanolamine (II) and 0.25% of amine or quaternary ammonium salt (Ia/Ib) and tested using the method specified in CEN 1275. The results are summarized in Table 1 below.

TABLE I

| Example No. | Amine/ammonium salt | Alkanolamine | $\log_{10}$ microbial reduction |
|---|---|---|---|
| 4 | dimethyldioctyl-ammonium chloride | monoethanolamine | 4.3 |
| 5 | dimethyldioctyl-ammonium chloride | diethanolamine | 4.0 |
| 6 | dimethyldioctyl-ammonium chloride | triethanolamine | 3.6 |
| 7 | dimethyldioctyl-ammonium chloride | 3-amino-1-propanol | 4.2 |
| 8 | didecyldimethyl-ammonium chloride | monoethanolamine | 4.0 |
| 9 | didecyldimethyl-ammonium chloride | diethanolamine | 3.8 |
| 10 | didecyldimethyl-ammonium chloride | triethanolamine | 3.1 |
| 11 | didecyldimethyl-ammonium chloride | 3-amino-1-propanol | 4.0 |
| 12 | di-$C_{8-10}$-alkyldimethyl-ammonium chloride (60%)/$C_{12-16}$-alkyl-benzyldimethylammonium chloride (40%); Bardac® 205-M | monoethanolamine | 3.9 |
| 13 | di-$C_{8-10}$-alkyldimethyl-ammonium chloride (60%)/$C_{12-16}$-alkyl-benzyldimethylammonium chloride (40%); Bardac® 205-M | diethanolamine | 3.2 |
| 14 | di-$C_{8-10}$-alkyldimethyl-ammonium chloride (60%)/$C_{12-16}$-alkyl-benzyldimethylammonium chloride (40%); Bardac® 205-M | triethanolamine | 2.8 |
| 15 | di-$C_{8-10}$-alkyldimethyl-ammonium chloride (60%)/$C_{12-16}$-alkyl-benzyldimethylammonium chloride (40%); Bardac® 205-M | 3-amino-1-propanol | 3.8 |
| 16 | N,N-bis(3-amino-propyl)dodecylamine | monoethanolamine | 2.9 |
| 17 | N,N-bis(3-amino-propyl)dodecylamine | diethanolamine | 2.7 |
| 18 | N,N-bis(3-amino-propyl)dodecylamine | triethanolamine | 2.4 |
| 19 | N,N-bis(3-amino-propyl)dodecylamine | 3-amino-1-propanol | 2.8 |

For comparison, all compounds listed in Table 1 were tested as individual substances in 0.5% strength solution. None of theses compounds exhibited pronounced fungicidal activity ($\log_{10}$ microbial reduction <2).

EXAMPLE 20

A disinfectant formulation (concentrate) was produced from:
9.9% didecyidimethylammonium chloride (70% strength solution)
8.0% monoethanolamine
5.0% Genapol® T250 (tallow fatty alcohol polyglycol ether, 25 mol of ethylene oxide)
5.0% potassium carbonate (anhydrous)

6.0% ethylenediaminetetraacetic acid tetrasodium salt (Trilon®B; 40% strength solution)
water to 100%

EXAMPLE 21

The concentrate described in Example 20 was tested in 6% strength dilution in the suspension test using an exposure time of 30, 60 and 120 minutes for effectiveness against poliovirus type 1 (Mahoney strain).
Test Method:

The test was performed in accordance with the "Richtlinie des Bundesgesundheitsamtes und der Deutschen Vereinigung zur Bekämpfung der Viruskrankheiten zur Prüfung von chemischen Desinfektionsmitteln auf Wirksamkeit gegen Viren" [Guideline of the German Federal Health Agency and the German Association for Controlling Viral Diseases for testing chemical disinfectants for effectiveness against viruses] (*Bundesgesundheitsbl*. 1982, 25, 397). The growth medium for the Vero cell cultures was "Dulbecco's Modified Eagle's Medium", to which 10% foetal calf serum and 10 U/ml of penicillin and also 10 µg/ml of streptomycin had been added. After the tissue culture was inoculated with poliovirus the tissue culture medium only contained 3% foetal calf serum. After virtually complete detachment of polio-infected cells, the virus suspension was purified by centrifuging of cells and cell constituents (3000×g, 15 min). Since the cell culture medium contained 3% foetal calf serum, in the disinfectant test also, a small protein load was also present in the test batches using twice-distilled water.

For the disinfectant test, 1 part of virus suspension was mixed with 8 parts of a 7.5% strength dilution of the disinfection concentrate (corresponding to a final concentration of 6%) and in each case 1 part of twice-distilled water or 2% strength serum albumin or foetal calf serum and was incubated for 30, 60 and 120 min at 20° C. The activity of the disinfectant was then stopped by 100-fold dilution with cold medium containing no foetal calf serum. In each case 2 wells of multiwell plates containing 6 recesses (Becton Dickinson Labware, Lincoln Park, N.J., Type Falcon™ 353046) which contained a dense lawn of Vero cells, were inoculated with 1 ml in each case of this dilution (corresponding to a dilution of the virus suspension to $10^{-3}$) and further serial 10-fold dilutions. After 1 h of adsorption time at room temperature, the supernatant liquid was drawn off. The cell lawns of the wells were then coated with 2 ml of 2% strength agarose (Serva high EEO, Cat. No. 11397) liquefied by boiling, which had been mixed with twice-concentrated medium containing 5% strength foetal calf serum in a ratio of 1:1, and had been cooled to 40° C. in a waterbath. After solidification of the agarose at room temperature, the plates were incubated for 2 days at 37° C. in a $CO_2$ incubation cabinet.

The infectivity of the virus suspension was tested in the plaque test. In this test each area of destroyed cells corresponds to one infectious unit of poliovirus. The number of plaques thus indicates the number of infectious virus particles present in a defined dilution of the test batch. The plaques are visualized by staining 1.0 ml in each case of a solution of 0.1% Brilliant Blue R (Sigma, Cat. No. B0149) for 30 min in an aqueous solution containing 20% methanol and 5% acetic acid. The unstained plaques are then clearly differentiated from blue-coloured cell lawns. A mean plaque count is calculated from two batches in each case of a dilution.

"Virus controls", in which the starting concentration of the virus was determined, were batches in which the disinfectant had been replaced by the same volume of twice-distilled water. The virus concentration thus determined served as reference for calculating the virus-inactivating action of the disinfectant tested. "Toxicity controls" for detecting any damage of the tissue culture cell by the disinfectant were batches in which the virus suspension had been replaced by the same volume of twice-distilled water. These batches were diluted in a ratio of 1:100 and 1:1000 (equivalent to a dilution of the virus suspension of $10^{-3}$ and $10^{-4}$ in the disinfectant test batch) with medium without foetal calf serum. Then they were added to the tissue culture, as with the batches for testing the disinfectant action, for 1 h and then drawn off. After incubation for 2 days at 37° C., staining was used to test whether the cell lawn had been damaged by the disinfectant.

As an indication of the resistance of the test virus and for comparability with other studies, a "formaldehyde control" was carried out. For this, 1 part of the virus suspension was mixed with 4 parts of phosphate-buffered saline (0.1 M; pH 7; "Dulbecco's PBS") and the entire volume was added to a formalin solution containing 1.4 g of formaldehyde in 100 ml of solution (final concentration: 0.79 of HCHO/100 ml). After 5, 15 and 60 min of exposure time, the action of formaldehyde was stopped, as with the disinfectant test, by diluting to 1:100 and the remaining infectivity of the poliovirus was determined in the plaque test in further serial ten-fold dilutions.
Results:
Control Experiments:

The "virus control", in the batch with twice-distilled water, gave a virus concentration of $1.6 \cdot 10^8$ infectious units/ml, in the batch containing serum albumin, $1.2 \cdot 10^8$ infectious units/ml, and in the batch containing foetal calf serum $1.0 \cdot 10^8$ infectious units/ml. The "toxicity control", after dilution of the test batch to 1:100 (equivalent to a dilution of the virus suspension of $10^{-3}$) showed slight damage of the cell lawn. At a dilution of 1:1000, toxicity was no longer observable. Thus under the test conditions, a decrease in virus concentration under the action of disinfectant can be followed to a virus concentration of $5 \cdot 10^3$ infectious units/ml in the virus suspension (in both wells of the dilution $10^{-4}$, plaque is then no longer visible) and at a starting concentration of at least $10^8$ infectious virus particles/ml, a decrease in virus concentration over at least 4.5 powers of ten is observable. Since the test guideline for detecting the effectiveness of a disinfectant only requires a decrease in virus concentration by at least 4 powers of ten, compliance with this condition can be detected using the experimental batch chosen. In the batch containing 0.7% strength formaldehyde, after an exposure time of 5 min, a virus concentration of $1.05 \cdot 10^6$/ml was measured, after 15 min $1 \cdot 10^3$/ml, and after 60 min $\leq 5 \cdot 10^2$/ml. These are expected values which confirm the results of earlier experiments: 0.7% strength formalin is usually able to reduce the concentration of poliovirus by more than 4 powers of ten within 30 min.
Effectiveness of the Disinfectants Against Poliovirus:

After 30, 60 and 120 min exposure times of 6% strength dilution of the disinfectant composition from Example 20, in the batch containing foetal calf serum at the virus dilution $10^4$, in each of the two test wells plaque was no longer observed. Thus after the disinfectant treatment, a virus concentration of $\leq 5 \cdot 10^3$ infectious units/ml was present. This result was found not only with low protein load (batch with twice-distilled water), but also with medium (batch containing 2% strength serum albumin) and high protein load (batch containing foetal calf serum). Thus, compared with the control determination without disinfectant, there was a decrease in virus concentration by at least 4.5 $\log_{10}$ or powers of ten.

Thus the condition for effectiveness for registration as instrument disinfectant in the Federal Republic of Germany is fulfilled.

EXAMPLE 22

Effectiveness Against ECBO Viruses:

The concentrate described in Example 20 was tested in accordance with the guideline of the (German) Federal Health Agency and the Deutsche Vereinigung zur Bekäimpfung der Viruskrankheiten e.V. for testing chemical disinfectants for effectiveness against viruses (*Bundesgesundheitsbl.* 1982, 25, 397-398; comment: *Bundesgesundheitsbl.* 1983, 26, 413414) in a quantitative suspension test for its virucidal properties against the ECBO virus strain LCR4. Tests were made of dilutions of 1.0%, 3.0% and 5.0% of the concentrate in twice-distilled water with exposure times of 15, 30, 60 and 120 min.

The test temperature was 20±1° C., and the protein load used was foetal calf serum (FCS) or serum albumin (bovine serum albumin, BSA).

To prepare the virus suspension, foetal calf lung cells (FCL 107) in Roux flasks containing minimum essential medium (MEM, Eagle) were infected with approximately 10 PFU (plaque forming units) of the virus (obtained by Dr W. Herbst, Institute for Hygiene and Infectious Animal Diseases at the Justus-Liebig University in Giessen) per cell and after appearance of the cytopathic effect (approximately 12 h), was subjected to three-fold freezing/thawing operation. There followed centrifugation at 770×g for 10 min which provided the virus suspension as supernatant.

To prepare the inactivation batches, 8 parts by volume of the disinfectant in the desired 1.25-fold concentration were mixed with virus suspension and twice-distilled water (1 part by volume each). In the experiments with protein load, instead of the twice-distilled water, one part by volume of FCS (Flow Laboratories) or 2% strength BSA solution (Behringwerke A G) were used.

The inactivation experiments were carried out in closed glass tubes. After the appropriate times, samples were withdrawn to determine the remaining infectivity.

The infectivity was determined using end-dilution titration in the micro method. For this the samples, immediately after they were taken, were diluted with minimum essential medium (MEM), with integral powers of ten being chosen as dilution factors. In each case 100 µl of a dilutes ample were transferred to 8 basins of a sterile polystyrene plate with a flat bottom. Then, in each case 100 µl of a freshly trypsinized suspension of KOP-R cells (cattle oesopharyngeal tissue, obtained from Dr R. Riebe, Bundesforschungsanstalt für Viruskrankheiten der Tiere auf der Insel Riems, Catalogue No. RIE 244) were added. This suspension was adjusted so that in each basin there were approximately 10–15×10³ cells. Thereafter the samples were incubated at 37° C. in a $CO_2$ incubation cabinet (5% by volume $CO_2$). After 5 to 7 days, the infectious dose ($ID_{50}$/ml) was determined by the method of Spearmann-Kärber.

The virucidal activity was determined by calculating the decrease in titre compared with the respective control titrations carried out in parallel (after the longest exposure time). The difference was reported as $\Delta\log_{10} ID_{50}$.

To determine the cytotoxicity of the disinfectant, 2 parts by volume of PBS (phosphate buffered saline) were mixed with 8 parts by volume of the disinfectant dilution (1.25-fold concentration), diluted correspondingly and applied to the cell cultures. The cytotoxic dose was reported as $\log_{10} CD_{50}$/ml (by analogy with the $ID_{50}$ value).

The results of the inactivation tests are summarized in Table 2 hereinafter, and those of the cytotoxicity determination in Table 3.

TABLE 2

| Concentration | Virus content (control) ($\log_{10}ID_{50}$/ml) | Protein load | Decrease in infection titre ($\Delta\log_{10}ID_{50}$) after | | | |
|---|---|---|---|---|---|---|
| | | | 15 min | 30 min | 60 min | 120 min |
| 1.0% | 6.85 | — | 1.25 | 1.25 | 1.64 | n.d. |
| 1.0% | 7.05 | 0.2% BSA | 1.00 | 1.25 | 1.34 | n.d. |
| 1.0% | 7.15 | 10.0% FCS | 1.00 | 1.15 | 1.25 | n.d. |
| 3.0% | 7.65 | — | ≧4.15 | ≧4.15 | ≧4.15 | ≧4.15 |
| 3.0% | 7.75 | 0.2% BSA | 3.45 | ≧4.25 | ≧4.25 | ≧4.25 |
| 3.00% | 7.65 | 10.0% FCS | 2.17 | 3.45 | ≧4.15 | ≧4.15 |
| 5.0% | 7.65 | — | ≧4.15 | ≧4.15 | ≧4.15 | ≧4.15 |
| 5.0% | 7.75 | 0.2% BSA | 4.05 | ≧4.25 | ≧4.25 | ≧4.25 |
| 5.0% | 7.65 | 10.0% FCS | 3.15 | ≧4.15 | ≧4.15 | ≧4.15 | n.d. = not determined

TABLE 3

| Concentration | Dilution step | | | | |
|---|---|---|---|---|---|
| | $10^{-1}$ | $10^{-2}$ | $10^{-3}$ | $10^{-4}$ | $10^{-5}$ |
| 1.0% | + | − | − | − | − |
| 3.0% | + | + | − | − | − |
| 5.0% | + | + | − | − | − |

The results show that the test composition (concentrate), at a usage concentration of 3.0%, after an exposure time of 60 min and at 5.0% after 30 min has the effectiveness defined in the guideline ($\Delta\log_{10}ID_{50} \geq 4.0$; equivalent to an inactivation of ≧99.99%) towards ECBO viruses.

EXAMPLE 23

Effectiveness Against Canine Parvovirus:

Dilutions of the concentrate described in Example 20 were tested for their effectiveness against canine parvovirus type 2 (obtained from Dr Parrish, Cornell University) in NLFK cells (Norden Lab Feline Kidney) at 22° C. and an exposure time of 10 min.

Dilutions in a ratio of 1:35 in demineralized or hard (400 ppm AOAC hard water) water containing 5% organic load (foetal calf serum) showed adequate virucidal effectiveness.

The invention claimed is:

1. A process of utilizing a disinfectant composition consisting of:
   a) an amine and/or quaternary ammonium salt of the general formula:

$$R^1 - N \begin{cases} (CH_2)_3NH_2 \\ (CH_2)_3NH_2 \end{cases} \quad (Ia)$$

or $$R^2 - \overset{R^3}{\underset{R^5}{N^+}} - R^4 \quad A^-, \quad (Ib)$$

where $R^1$ is $C_{6-18}$-alkyl,
$R^2$ is benzyl or $C_{6-18}$-alkyl,
$R^3$ is $C_{1-18}$-alkyl or —[(CH$_2$)$_2$—O]$_n$R$^6$ where n=1-20,
$R^4$ and $R^5$ independently of one another are $C_{1-4}$-alkyl,
$R^6$ is hydrogen or unsubstituted or substituted phenyl, and
$A^-$ is a monovalent anion or one equivalent of a polyvalent anion of an inorganic or organic acid;
b) at least one alkanolamine of the general formula:

$$HO-(CH_2)_n-N \begin{matrix} [(CH_2)_m-O]_x-H \\ [(CH_2)_o-O]_y-H, \end{matrix} \quad (II)$$

where n and, if present, m and O independently of one another have the value 2 or 3, and
x and y independently of one another have the value 0 or 1, or a corresponding salt;
in the mass ratio a):b) of 20:1 to 1:20; and
c) water, as solvent.

2. The process according to claim 1, wherein the amine or quaternary:ammonium salt is selected from the group consisting of N,N-bis-(3-aminopropyl)dodecylamine, N,N-bis (3-aminopropyl)octylamine, didecyldimethylammonium salts, dioctyldimethylammonium salts, octyldecyldimethylammonium salts, cocoalkyldimethylbenzylammonium salts and benzyldimethyloxoethylammonium salts and mixtures of these compounds.

3. The process according to claim 1, wherein the alkanolamine b) is selected from the group consisting of monoethanolamine, diethanolamine, triethanolamine and 3-amino-1-propanol.

4. The process according to claim 1, wherein the mass ratio a):b) is between 1:5 and 5:1.

5. A process according to claim 1, wherein the virucidal agent of claim 1 is utilized for surface disinfection and instrument disinfection.

6. A process according to claim 1, wherein the virucidal agent of claim 1 is utilized for laundry disinfection.

7. A process according to claim 1, wherein the virucidal agent of claim 1 is utilized for hand disinfection.

8. A process according to claim 1, wherein the virucidal agent of claim 1 is utilized for chemical toilets.

9. A process wherein the virucidal agent of claim 1 is utilized against parvoviruses, picornaviruses or polioviruses.

10. The process according to claim 2, wherein the alkanolamine b) is selected from the group consisting of monoethanolamine, diethanolamine, triethanolamine and 3-amino-1-propanol.

11. The process according to claim 2, wherein the mass ratio a):b) is between 1:5 and 5:1.

12. The process according to claim 3, wherein the mass ratio a):b) is between 1:5 and 5:1.

13. The process according to claim 10, wherein the mass ratio a):b) is between 1:5 wad 5:1.

14. A process wherein the virucidal agent according to claim 2 is utilized for surface disinfection and instrument disinfection.

15. A process wherein the virucidal agent according to claim 2 is utilized for laundry disinfection.

16. A process wherein the virucidal agent according to claim 2 is utilized for hand disinfection.

17. A process wherein the virucidal agent according to claim 2 is utilized for chemical toilets.

18. A process wherein the virucidal agent according to claim 2 is utilized against parvoviruses, picornaviruses or polioviruses.

19. A process consisting of utilizing a disinfectant composition consisting of:
a) an amine and/or quaternary ammonium salt of the general formula:

$$R^1-N \begin{matrix} (CH_2)_3NH_2 \\ (CH_2)_3NH_2 \end{matrix} \quad \text{or} \quad (Ia)$$

$$R^2-\underset{R^5}{\overset{R^3}{\underset{|}{\overset{|}{N^+}}}}-R^4 \quad A^-, \quad (Ib)$$

where $R^1$ is $C_{6-18}$-alkyl,
$R^2$ is benzyl or $C_{6-18}$-alkyl,
$R^3$ is $C_{1-18}$-alkyl or —[(CH$_2$)$_2$—O]$_n$R$^6$ where n=1-20,
$R^4$ and $R^5$ independently of one another are $C_{1-4}$-alkyl,
$R^6$ is hydrogen or unsubstituted or substituted phenyl, and
$A^-$ is a monovalent anion or one equivalent of a polyvalent anion of an inorganic or organic acid;
at least one alkanolamine of the general formula:

$$HO-(CH_2)_n-N \begin{matrix} [(CH_2)_m-O]_x-H \\ [(CH_2)_o-O]_y-H, \end{matrix} \quad (II)$$

where n and, if present, m and o independently of one another have the value 2 or 3, and
x and y independently of one another have the value 0 or 1, or a corresponding salt;
in the mass ratio a):b) of 20:1 to 1:20;
c) water; as solvent; and
d) one or more auxiliaries selected from the group consisting of organic solvents, surfactants, complexing agents, fragrances and colorants.

20. A process utilizing a disinfectant composition consisting of:
a) an amine and/or quaternary ammonium salt of the general formula:

$$R^1-N \begin{matrix} (CH_2)_3NH_2 \\ (CH_2)_3NH_2 \end{matrix} \quad \text{or} \quad (Ia)$$

$$R^2-\underset{R^5}{\overset{R^3}{\underset{|}{\overset{|}{N^+}}}}-R^4 \quad A^-, \quad (Ib)$$

where $R^1$ is $C_{6-48}$-alkyl,
$R^2$ is benzyl or $C_{6-18}$-alkyl,
$R^3$ is $C_{1-18}$-alkyl or —[(CH$_2$)$_2$—O]$_n$R$^6$ where n=1-20,
$R^4$ and $R^5$ independently of one another are $C_{1-4}$-alkyl, $R^6$ is hydrogen or unsubstituted or substituted phenyl, and
$A^-$ is a monovalent anion or one equivalent of a polyvalent anion of an inorganic or organic acid;

b) at least one alkanolamine of the general formula:

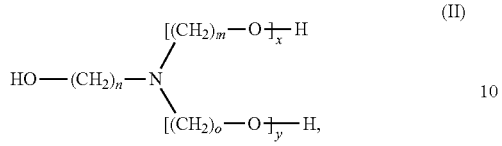

(II)

where n and, if present, m and o independently of one another have the value 2 or 3, and x and y independently of one another have the value 0 or 1, or a corresponding salt;

in the mass ratio a):b) of 20:1 to 1:20;

c) water, as solvent; and d) one or more auxiliaries selected from the group consisting of organic solvents, surfactants, complexing agents, fragrances and colorants.

\* \* \* \* \*